United States Patent [19]

Colon

[11] Patent Number: 5,460,787
[45] Date of Patent: * Oct. 24, 1995

[54] APPARATUS AND METHOD FOR PROVIDING A SCENT

[76] Inventor: Amber M. Colon, 604 Holly Dr., Edmond, Okla. 73034

[ * ] Notice: The portion of the term of this patent subsequent to Jun. 6, 2012 has been disclaimed.

[21] Appl. No.: 335,023

[22] Filed: Nov. 7, 1994

Related U.S. Application Data

[63] Continuation of Ser. No. 834,910, Feb. 13, 1992.

[51] Int. Cl.⁶ .................................................. A61L 9/00
[52] U.S. Cl. ..................... 422/123; 55/279; 55/504; 422/4; 239/55
[58] Field of Search ........................ 422/123, 4; 55/279, 55/504; 239/55; 261/DIG. 65; 428/905

[56] References Cited

U.S. PATENT DOCUMENTS

| | | | |
|---|---|---|---|
| Re. 33,864 | 3/1992 | Steiner et al. | 261/30 |
| 1,385,502 | 7/1921 | Smith | 239/57 |
| 1,742,613 | 1/1930 | Moore et al. | 239/57 |
| 1,801,949 | 4/1931 | Broudy et al. | 239/57 |
| 3,844,478 | 10/1974 | Davis | 239/57 |
| 3,902,877 | 9/1975 | Swaim | 55/279 |
| 4,028,073 | 6/1977 | Swaim | 55/279 |
| 4,065,262 | 12/1977 | Petroff | 21/74 R |
| 4,095,031 | 6/1978 | Engle | 239/58 |
| 4,118,226 | 10/1978 | Bourassa | 55/279 |
| 4,166,565 | 9/1979 | Webinger | 229/8 |
| 4,257,787 | 3/1981 | Taylor | 55/279 |
| 4,306,892 | 12/1981 | Atalla et al. | 55/279 |
| 4,411,055 | 10/1983 | Fiebig, Jr. | 264/219 |
| 4,476,171 | 10/1984 | Takeuchi | 428/38 |
| 4,563,333 | 1/1986 | Frigon | 422/122 |
| 4,604,114 | 8/1986 | Ward | 55/279 |
| 4,617,157 | 10/1986 | Stein et al. | 261/96 |
| 4,676,954 | 1/1987 | Wilson | 422/124 |
| 4,689,058 | 8/1987 | Vogt | 55/279 |
| 4,944,898 | 7/1990 | Glaser | 261/84 |
| 5,019,434 | 5/1991 | Matsumoto | 428/35.7 |
| 5,141,707 | 8/1992 | Brite | 422/124 |

*Primary Examiner*—Timothy M. McMahon
*Assistant Examiner*—N. Bhat
*Attorney, Agent, or Firm*—Dunlap & Codding

[57] ABSTRACT

An apparatus and method for providing a scent to a compartment comprising a reusable holder having a connecting means and a scented card insertable into the holder. The connecting means can be a clip which is connectable to a louver of an air duct outlet register of a forced air system or to a fan guard of a utility fan. The apparatus can also be modified to attach to an interior surface of a refrigerator and may even be adaptable for use as costume jewelry. The scented card is produced by a process wherein a heat extrudable thermoplastic material is mixed with a chemical blowing agent and at least one fragrance and optionally a coloring agent, the mixture of material and fragrance is heated and extruded to produce a flat fragrant sheet of material which after being trimmed, forms a relatively rigid but flexible card insertable into the holder and removable therefrom.

48 Claims, 4 Drawing Sheets

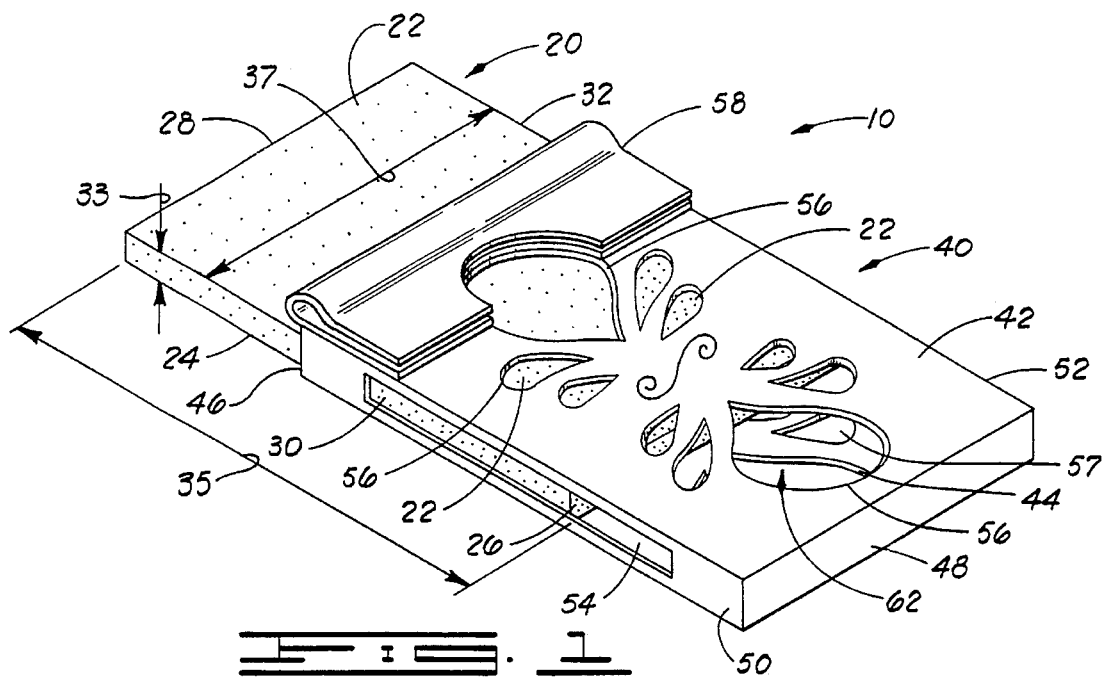
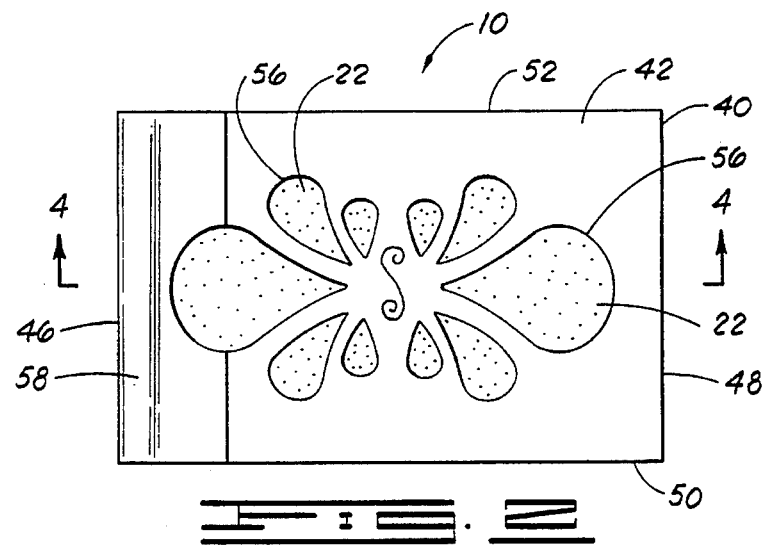
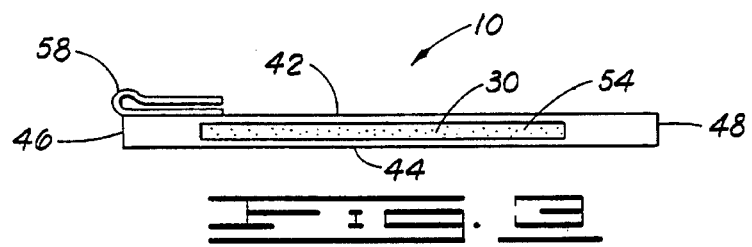
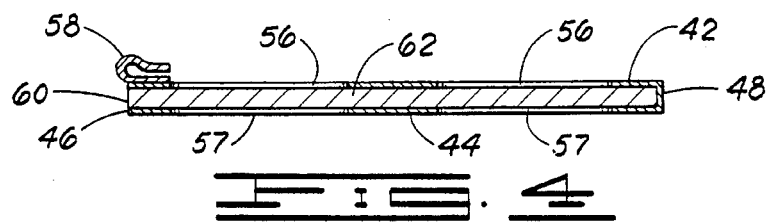

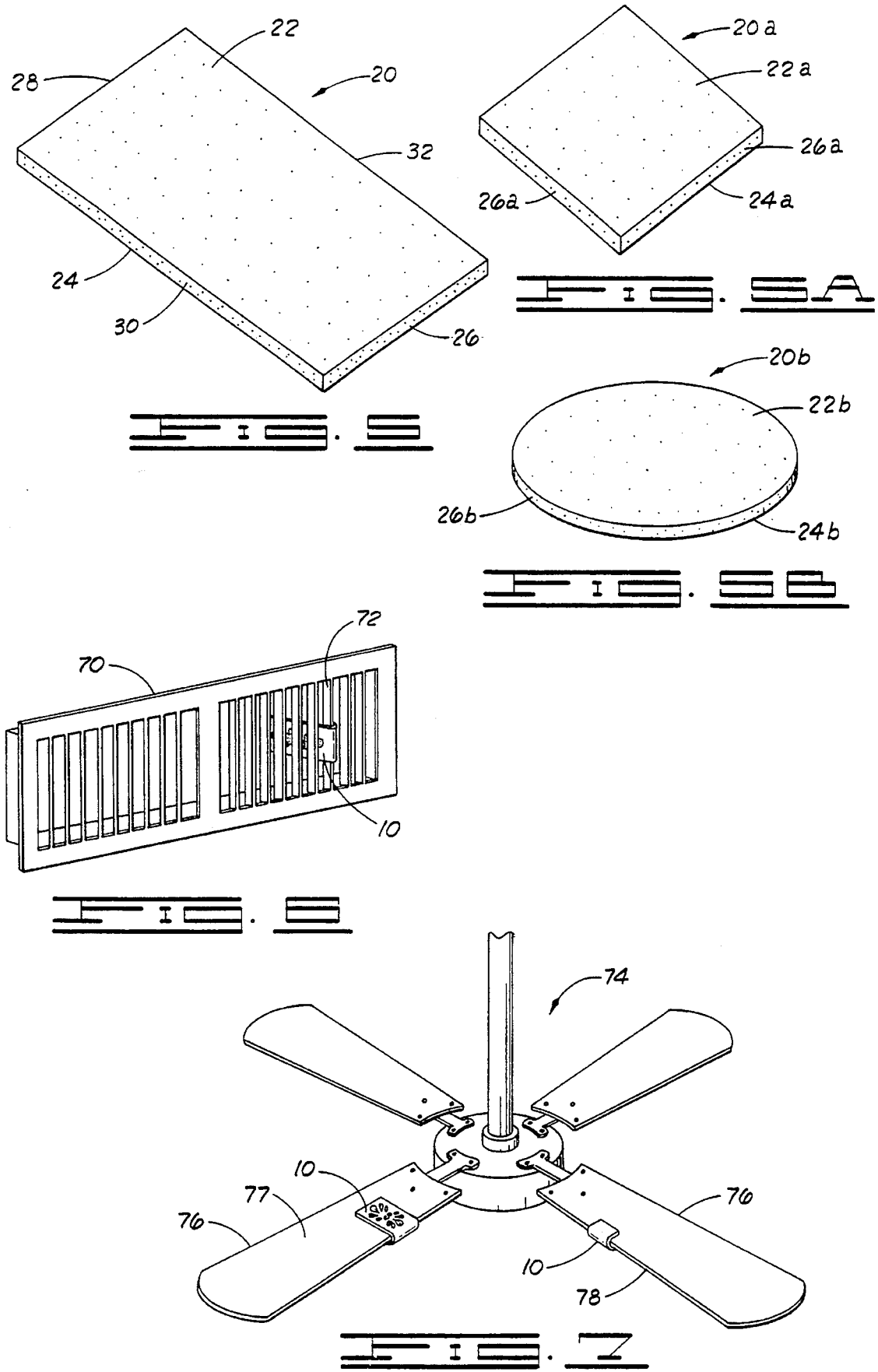

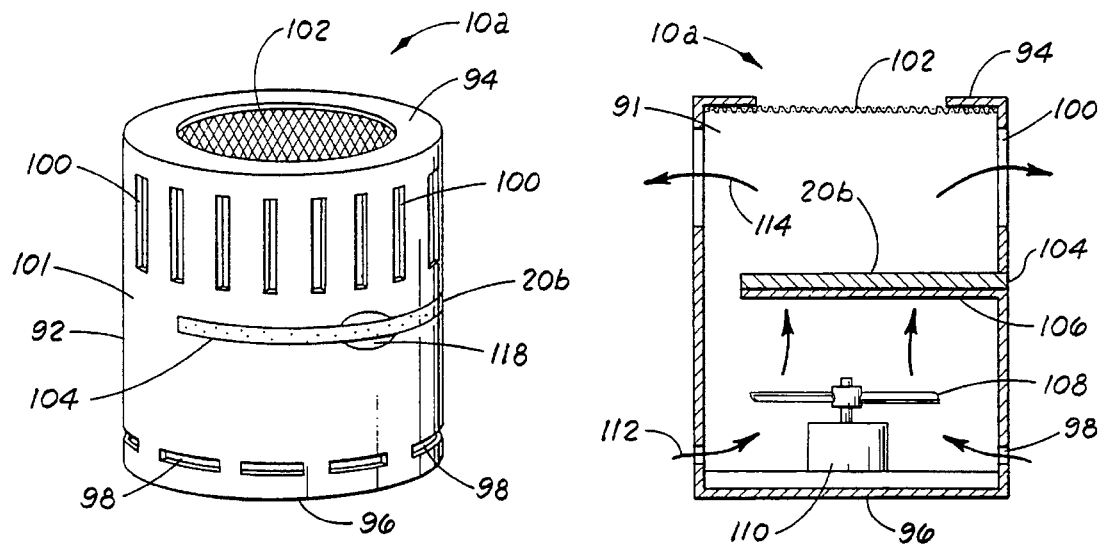
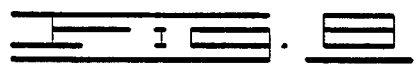 
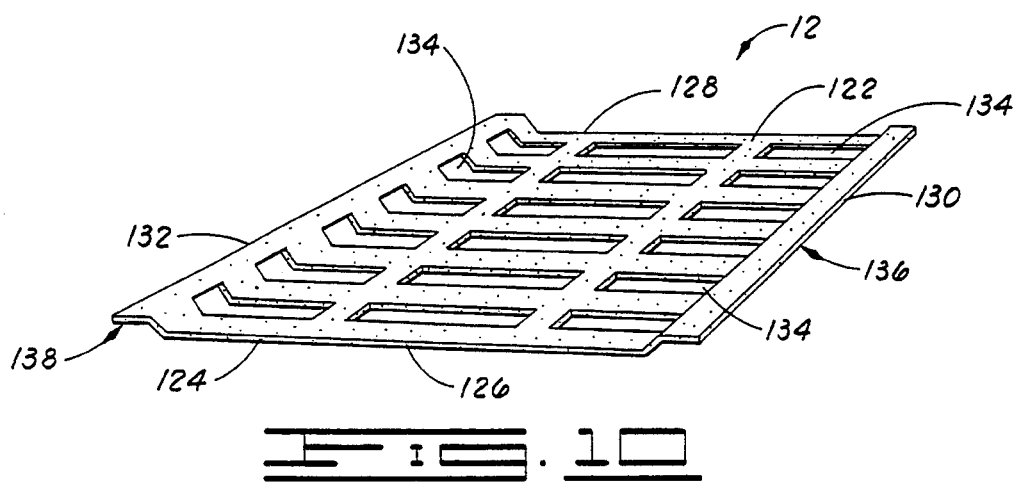
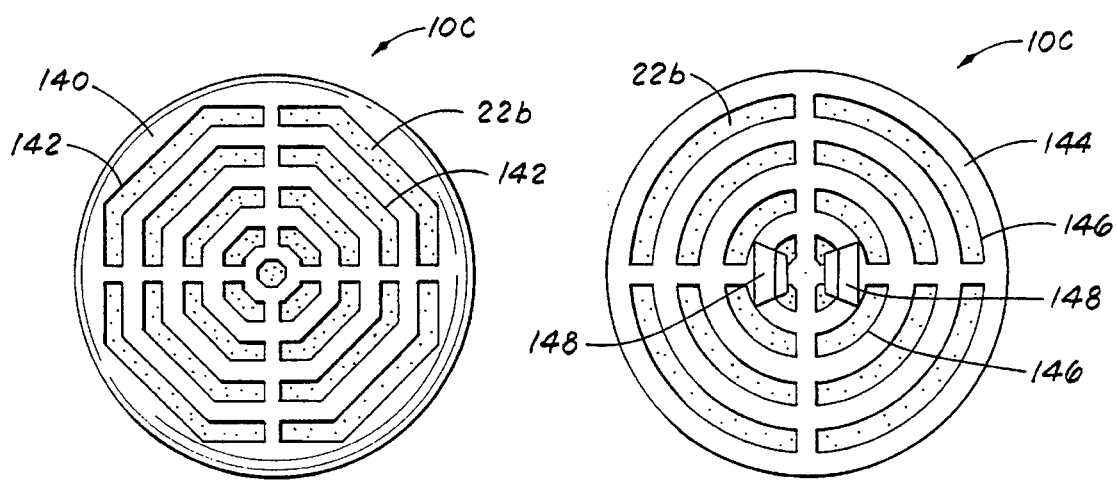
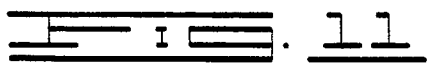 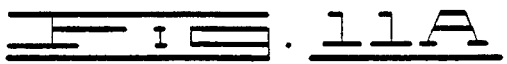

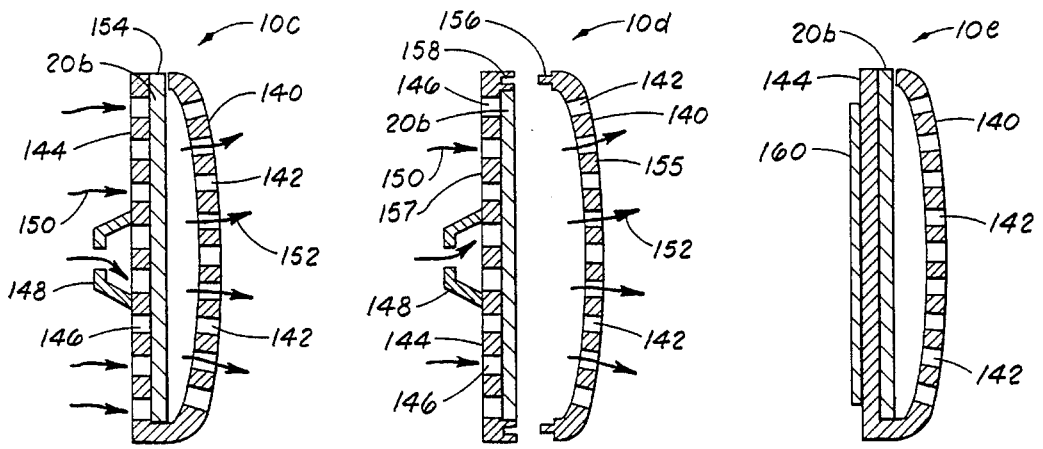
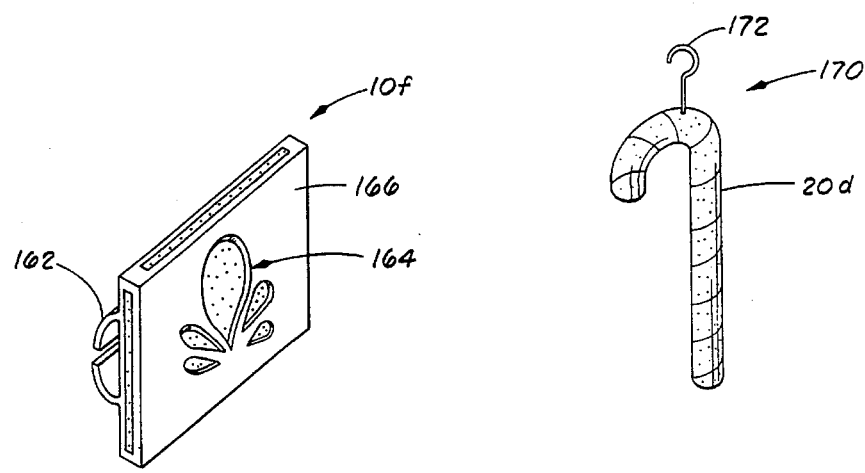
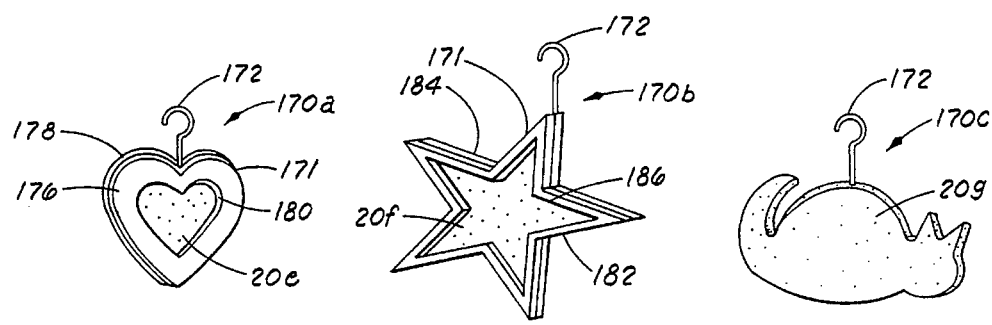

5,460,787

APPARATUS AND METHOD FOR PROVIDING A SCENT

"This is a continuation of copending application Ser. No. 07/834,910 filed on Feb. 1992."

BACKGROUND OF THE INVENTION

1. Field of the Invention

This invention relates to devices used to provide a scent, and more particularly, but not by way of limitation, to devices used to provide a scent to a specific confined area in combination with a forced air flow.

2. Brief Description of the Related Art

There are a variety of circumstances which make it desirable to provide a scent or fragrance to a particular area. For example, rooms, kitchens, offices or enclosed compartments such as closets or vehicle interiors may acquire odors which are wished to be dispelled or otherwise masked. Devices known as air fresheners which utilize spray applicators or which are placed on an open surface in a room are widely available to provide such a scent. Spray applicators require manual assistance whenever their use is desired. Stationary, devices, although not requiring manual assistance after initial installation, must be replaced rather frequently and are not equipped with a means for distributing the fragrance about the space except by ambient air movement, resulting in an uneven distribution of fragrance about the room. Moreover, regular use and replacement of the devices or sprays can generate a significant accumulation of refuse over time contributing to the solid waste problem.

Another method-which is available to provide a fragrance to a room is to attach a packet of fragrance to the input air filter of a heating or air conditioning system whereby the air flowing over the filter is treated with the fragrance from the fragrance packet. The air is distributed to all compartments served by the system thereby treating the air in all compartments without having to treat the rooms on an individual basis. This method suffers from at least two drawbacks in that individual rooms or compartments are prevented from being treated separately (all rooms must have the same scent) and in general the air freshening packets commercially available have a rather short effective life because the fragrance is supplied by felt pad or by some other porous material which has been saturated with the fragrant oil. In another method the fragrance is provided by a cake of material which is designed to release its fragrance by sublimation of the cake as air passes over it. Thus the cake (which may be comprised of a gel or gel-like material) gradually evaporates until only a residue is left. Air treatment methods which are attached to the intake filter of a forced air system further tend to suffer effects of dust fouling wherein dust accumulates on the air treatment device thus reducing its ability to release fragrance.

It can be seen from the foregoing that current methods of providing a fragrance to the air in an area suffer from a number of drawbacks which limit their applicability or usefulness in particular situations. It is the particular object of the present invention described herein to overcome these limitations and drawbacks thereby improving and enhancing the manner in which fragrance is provided to an area.

BRIEF DESCRIPTION OF THE DRAWINGS

FIG. 1 is a perspective view of the scenting apparatus showing a scented card partially inserted into the card holder.

FIG. 2 is a plan view of the apparatus shown in FIG. 1 with the card fully inserted into the card holder.

FIG. 3 is a side elevational view of the apparatus shown in FIG. 1.

FIG. 4 is a side cross-sectional view taken through the planes shown as lines 4—4 on FIG. 2.

FIG. 5 is a perspective view of a scented card having a rectangular shape.

FIG. 5A is a perspective view of a scented card having a square shape.

FIG. 5B is a perspective view of a scented card having a circular shape.

FIG. 6 is a perspective view of the apparatus of FIG. 1 clipped to a louver of an air duct register.

FIG. 7 is a perspective view of the apparatus of FIG. 1 clipped in two manners to blades of a ceiling fan.

FIG. 8 is a perspective view of an alternative embodiment of the scenting apparatus.

FIG. 9 is a side cross-sectional view of the apparatus of FIG. 8 indicating the fan and fan drive means within the apparatus.

FIG. 10 is a perspective view of an alternative embodiment of the apparatus designed for use as a refrigerator shelf.

FIG. 11 is a front elevational view of an alternative embodiment of the scenting apparatus.

FIG. 11A is a rear elevational view of the apparatus shown in FIG. 11.

FIG. 12 is a side cross-sectional view of the apparatus shown in FIGS. 11 and 11A.

FIG. 12A is a side cross-sectional view of an alternative embodiment of the apparatus in FIGS. 11 and 11A in which the front side is detachable from the rear side.

FIG. 12B is a side cross-sectional view of an alternative embodiment of the apparatus shown in FIG. 11 wherein the attaching means is a flat adhesive surface rather than a clip.

FIG. 13 is a perspective view of an alternative embodiment of the scenting apparatus.

FIG. 14 is a perspective view of a piece of costume jewelry comprised of the scented card material of the present invention.

FIG. 14A is a perspective view of a piece of costume jewelry containing a scented card.

FIG. 14B is yet another example of a piece of costume jewelry containing a scented card.

FIG. 14C is yet another example of a piece of costume jewelry comprised of the scented card material of the present invention.

BRIEF DESCRIPTION OF THE INVENTION

The invention described herein comprises an apparatus and method for providing a scent to an area. The invention includes a novel material derived from a thermoplastic copolymer resin within which is entrapped a fragrance. The processed fragrant thermoplastic material is cut, trimmed or otherwise formed into relatively rigid, but flexible shapes adaptable to a variety of uses and circumstances. In a preferred embodiment, the scented material is shaped into a flat rectangular card insertable into a holder having a connecting means, such as a clip, for connecting the holder to a louver of an air duct register of a forced air blowing assembly such as a heating and air conditioning system. As air is forced through the air duct by the air blowing means of the forced air system, it is scented with the fragrance contained within the scented card held within the card holder as the fragrance volatilizes from the card. The room, office, or compartment thus becomes scented with the fragrance. Each time the forced air system is reactivated, the fragrance within the room is renewed.

Because the present apparatus is attached to a ducted outlet portion of a forced air system rather than to the air inlet, individual rooms, offices or compartments such as vehicle interiors, elevators, storage areas, basements, hallways, closets, kitchens, restrooms or bathrooms, or similar areas serviced by the air distribution system may be scented with different fragrances or may be left unscented. Other air scenting methods or devices which are integrated with forced air systems do not allow this flexibility or ease of operation because they are typically attached to the inlet filter of the system and thus distribute scent to all rooms or compartments serviced by the system.

Another advantage of the present invention is ease of application. The holder with the scented card inserted is simply clipped to an air duct register. The apparatus is thus out of view and out of the reach of small children who may be tempted to touch, grab, hold, chew, carry off or otherwise manipulate the apparatus. Moreover, since the apparatus is attached to an air duct register louver, valuable area on surfaces such as table tops, shelves, ledges, or sills need not be occupied as would be the case for stationary air fresheners which must rest upon lateral surfaces. This not only serves to reduce the clutter within a room but also eliminates the concern one might have regarding the visual appeal of such other air fresheners or how well they integrate into the overall appearance of the room, office or compartment. Additionally, the present invention, being of a small and flat size which could easily be grasped in one's hand, will generate less solid waste. In particular, since the scented card is removable from the holder, when the scent has diminished, only the scented card need be replaced. The holder is reusable and thus need not necessarily be disposed. It is notable that certain other scent providing substances such as cakes, gels and other semi-solid materials are not nearly so adaptable to easy removal and insertion and thus the opportunities for reuse of such materials and holders of such materials are very limited, unlike the present invention.

It will be seen that the card holder and the scented thermoplastic material novel to this invention is adaptable to a variety of other scent-providing embodiments. For example, the card holder and connecting means could be modified to make the apparatus connectable, for example by a clip, to the protective guard of a fan assembly having a guard and fan-blade such as an oscillating fan or utility fan. The connecting means could also be an adhesive backing allowing the card holder to be connectable to the interior wall of a refrigerator compartment. In another embodiment, the scented card can be inserted into the housing of a portable fandriven device having a solar, battery or electric-powered motor which could serve to provide a scent to an area such as an office or waiting room. In another example, the connecting means of the card-holder apparatus could be modified to be connectable by clipping to the shelf or other surface within the interior of a refrigerator for the purpose of scenting or deodorizing the interior of the refrigerator. The scented thermoplastic material could be further modified to be formed into the shape of an actual refrigerator shelf which would function not only to support items within the compartment but also to deodorize and freshen the air within the compartment. Other confined areas such as vehicle interiors could also benefit from the scenting properties of the apparatus if the holder was adapted to be connectable to surfaces found in vehicles, such as the louvers on an air conditioning and heating outlet on an automobile dashboard. Finally, it will be seen that due to its scent-providing properties, the scented thermoplastic material is easily adaptable to its use in various types of costume jewelry such as finger rings, ear rings, bracelets, necklaces, charms, hair pins, hair barrettes, brooches, and lapel buttons and other types of costume jewelry or any combination of these which would be attractive to young persons as a fad item.

DESCRIPTION OF THE PREFERRED EMBODIMENTS

Embodiment of FIGS. 1–7

Shown in FIGS. 1–4 is an apparatus 10 for providing a scent. The apparatus 10 comprises a card 20 having scent incorporated therein and having a substantially flat upper surface 22, a substantially flat lower surface 24, a first end side 26, a second end side 28, a first lateral side 30, and a second lateral side 32. In the preferred embodiment, the scented card 20 has a thickness 33 extending between the upper and lower surfaces 22 and 24 in the range of from one-thirty secondths of an inch to three-sixteenths of an inch, a length 35 extending between the first end side 26 and the second end side 28 in the range of from three inches to four and one-half inches and a width 37 extending between the first lateral side 30 and the second lateral side 32 in the range of from one and one-half inches to two and one-half inches. The apparatus 10 further comprises a rectangular box-shaped card holder 40 having an upper surface 42, a lower surface 44, a first end 46, a second end 48, a first lateral side 50, and a second lateral side 52. The card 20 is insertable into the holder 40 and removable therefrom so the card 20 may be replaced when the scent no longer is being emitted from the card 20. The card 20 is relatively rigid, but flexible.

The holder 40 further comprises a slot 54 in the first lateral side 50, a similar slot (not shown) in the second lateral side 52, an opening 56 in the upper surface 42, an opening 57 in the lower surface 44, a clipping or connecting means 58 connected to the holder 40 for removably connecting the holder 40 to an object, an end slot 60 in the first end 46, and an interior space 62 substantially encompassed by the holder 40.

The slot 60 in the preferred embodiment has a length extending between the first lateral side 50 and the second lateral side 52 in the range of from one and three-fourths inches to two and three-fourths inches and a height in the range of from one-sixteenth of an inch to one-fourth of an inch, such that the width 37 of the card 20 is less than the length of the slot 60 and the thickness 33 of the card 20 is less than the height of the slot 60. The space 62 in the preferred embodiment has a length in the range of from three to four and one-half inches, a width in the range of from one and three-fourths inches to two and three-fourths inches and a height in the range from one-sixteenth of an inch to one-fourth of an inch.

FIG. 2 shows a frontal view of the surface 42 of the holder 40 wherein the upper surface 22 of the card 20 is shown fully inserted into the holder 40. FIG. 3 is a side elevational view of the apparatus 10. FIG. 4 is a side cross-sectional view of apparatus 10.

Shown in FIGS. 5, 5A and 5B are three embodiments of cards which may be inserted into various embodiments of apparatus 10. FIG. 5 shows the rectangular card 20 as described previously. FIG. 5A shows a square card 20a having an upper surface 22a, a lower surface 24a and equal lateral sides 26a. Shown in FIG. 5B is a round card 20b having an upper surface 22b, a lower surface 24b, and a peripheral side 26b, which would be adaptable for use in the scent providing embodiment of FIG. 8 and 9 described below. It will be understood by those skilled in the art that numerous other geometric, asymmetric and fanciful shapes of cards are conceivably useful in various situations. For example, other cards may be in the shape of a triangle, an oval, an ellipse, a trapezoid, a star and a parallelogram, wherein the card holder is of a shape adapted to hold a card with such a shape.

Shown in FIG. 6 is one example of how the apparatus 10 is attached to the register 70 of an air outlet duct (not shown). The apparatus 10 is clipped on a louver 72 of the air duct register 70 wherein air flowing through the air outlet duct and out the air duct register 70 is treated by the fragrance emitted from the card 20 of the apparatus 10 wherein air flowing through the air duct register 70 is distributed throughout the room.

FIG. 7 shows a ceiling fan 74 having a plurality of ceiling fan blades 76, each ceiling fan blade 76 having an upper surface 77 and a lower surface 78. The apparatus 10 can be clipped as indicated in FIG. 7 to the upper surface 77 of a fan blade 76 or to the lower surface 78 of a fan blade 76 wherein the scent within the apparatus 10 is distributed to the ambient air as the blades 76 of the ceiling fan 74 rotate.

Embodiments of FIGS. 8 and 9

FIG. 8 shows an apparatus 10a which is a portable scenting blower device. The apparatus 10a is designed to be placed on a desk (not shown) or other surface in an office or room, for example a waiting room, for scenting the ambient air within the office or the room.

The apparatus 10a is comprised of a housing 92 which has an upper end 94 and a lower end 96. A plurality of air in-take vents 98 are arranged along the lower end 96 of the housing 92. A plurality of air out-flow vents 100 are distributed about an outer peripheral surface 101 of the housing 92 near the upper end 94. An arrangement of solar cells 102 is located in the upper end 94 for the purpose of providing power.

The housing 92 includes a card insertion slot 104 formed through the outer peripheral surface 101 between the upper end 94 and the lower end 96 through which the card 20b is inserted. To facilitate the removal of the card 20b from the housing 92, an indention 118 is formed across the card insertion slot 104. The card 20b is supported on a support surface 106 within the interior space 91 of the housing 92, the interior space 91 being substantially encompassed by the housing 92.

FIG. 9 is a vertical cross-sectional view through apparatus 10a. The apparatus 10a includes a fan 108 driven by a fan-drive means 110 for the purpose of circulating air within space 91 of the apparatus 10a. The fan-drive means 110 is powered by solar cells 102. In alternative embodiments, the fan may be driven by battery means (not shown), by AC electricity means (not shown) or even by a gas-powered means (not shown). The fan 108 draws air from the outside through the air in-take vents 98 in the direction 112 and circulates the air past the card 20b in the direction 114 where air flows out of the apparatus 10a through air out-flow vents 100 after the air has volatilized fragrance from the card 20b. The card 20b is removable from the housing 92.

Embodiment of FIG. 10

FIG. 10 shows an article having a predetermined shape or, more particularly, a refrigerator shelf 12 which is formed from a scented sheet of material which includes a fragrant scent or a fragrant deodorizing material for the purpose of scenting or deodorizing the air within a refrigerator compartment (not shown). The shelf 12 is comprised of an upper surface 122, a lower surface 124, a first end 126, a second end 128, a first lateral side 130 and a second lateral side 132. The shelf 12 has a plurality of slots 134 which extend through the upper surface 122 open to the lower surface 124. The shelf 12 has a first lateral 136 arm which is elevated above the shelf surface and a second lateral arm 138 which is elevated above the shelf surface 122 which allows the shelf 12 to rest on support means (not shown) of the interior refrigerator wall for the purpose of supporting the shelf 12. The shelf 12 may be reinforced with reinforcing bars (not shown) composed of a rigid material such as metal or plastic which serve to provide additional strength to the shelf 12.

Embodiments of FIGS. 11–13

FIG. 11 shows an article having a predetermined shape or, more particularly, a clip-on scenting apparatus 10c which is designed to connect to surfaces which do not accept the connecting means 58 of apparatus 10. The apparatus 10c for example could be designed to clip on the bars of a refrigerator shelf or to the bars of the guard of a utility or oscillating fan. A utility fan will be understood to be a portable or movable fan which has a purpose of forcing air movement within a given area, such as a room or hallway. An oscillating fan is a utility fan capable of changing by rotation its direction of air movement.

The apparatus 10c has an upper surface 140 within which are arranged a plurality of slots 142. FIG. 11 shows the slots 142 arranged in a pattern of concentric octagons. As shown in FIG. 11A, the apparatus 10c has a lower surface 144 within which are arranged a plurality of slots 146 formed in the shape of concentric circles. However, it will be apparent that any number of geometric patterns of slots 142 in the upper surface 140 or slots 146 in the lower surface 144 would be feasible for the purpose of ventilating the apparatus 10c. For example, the pattern could be a series of concentric pentagons, hexagons, triangles, or even a plurality of discrete geometrically-shaped openings in the surface such as independent squares, stars or circles or combinations of these. The pattern could also be a fanciful decoration similar to that of the opening 56 indicated on apparatus 10.

A connecting means 148 is arranged on the lower surface 144 of the apparatus 10c for the purpose of clipping or connecting the apparatus 10c on to an object capable of receiving the connecting means.

A side cross-sectional view of the apparatus 10c is shown in FIG. 12. FIG. 12 indicates the plurality of slots 142 in the upper surface 140 and a plurality of slots 146 in the lower surface 144. Air flows through the slots 146 in the direction 150 into the interior of the apparatus 10c wherein is located a card 20b which has been inserted into a slot 154. Scented air flows out of the apparatus 10c through the slots 142 in the upper surface 140 in the direction 152 for the purpose of scenting the compartment within which is located the apparatus 10c.

FIG. 12A shows a modified clip-on apparatus 10d which is constructed exactly like the apparatus 10C, except the apparatus 10d includes an upper part 155 attachable to and detachable from the lower part 157 by an engaging means 156 in the upper part 155 which is engageable with a notch 158 in the lower part 157 for the purpose of attaching and reattaching the upper part 155 to the lower part 157. In the embodiment of the apparatus 10d, the card 20b is insertable into the apparatus 10d by detaching the upper part 155 from the lower part 157 wherein the card 20b is placed up against the lower part 157 and the upper part 155 is reattached to the lower part 157 by the engaging means 156 which is engagingly engaged with the notch 158 in the lower part 157.

FIG. 12B shows a further embodiment of the apparatus 10e. Apparatus 10e has an adhesive backing 160 which serves as a connecting means and which may connect the apparatus 10e to an interior wall of a refrigerator, for example. Additionally the lower surface 144 of the apparatus 10e may not have air in-flow slots 146 as indicated in FIG. 12B or may have air in-flow slots (not shown) in another embodiment in which the slots surround the adhesive backing 160.

Indicated in FIG. 13 is another version of the apparatus in which the apparatus 10f is a modified clip-on apparatus 10f having a clipping means 162 and a decoratively designed opening 164 in the upper surface 166 of the apparatus 10f. The clip-on scenting apparatus 10f could serve the function of attaching to a clip-on surface (not shown) in an automobile or could even clip-on to a piece of clothing (not shown) for the purpose of providing an attractive scent.

Embodiments of FIGS. 14–14C

A further embodiment of the apparatus could be in the form of an article having a predetermined shape or, more particularly, costume jewelry as indicated in FIGS. 14–14C. In these figures are indicated the scent providing materials which are shaped in various decorative and fanciful shapes such as a candy cane 20d, a heart 20e, a star 20f, and a cat 20g. These figures are merely a sample of the innumerable decorative and fanciful shapes and patterns which could comprise jewelry or charms. In FIG. 14 is indicated a candy cane shaped piece of jewelry 170 having an attaching means 172, the attaching means 172 could be an earlobe hook or a means to attach the jewelry 172 to a bracelet such as a charm bracelet (not shown).

In a similar manner FIG. 14A indicates a piece of heart shaped jewelry 170a containing a heart shape card 20e within the holder of 170a. The holder 171 comprises an upper surface 176 and a lower surface 178 and an opening 180 through the upper surface 176 and the lower surface 178, the card 20e thereby being visible through the opening 180. As previously mentioned for the embodiment 170 in FIG. 14, the piece 170a could be either an earring attachable by attaching means 172 which could be a hook or attachable to a charm bracelet (not shown) by an attaching means 172 which could be a clasp.

FIG. 14B shows a piece of jewelry 170b having the shape of a star. The jewelry 170b could be an earring attachable by a clasp or by a hook 172 or it could be a charm attachable by a clasp means 172 to a charm bracelet (not shown). The jewelry 170b comprises a holder 171 having an upper surface 182, a lower surface 184 and a opening 186 through the upper surface 182 and the lower surface 184 through which is visible the star shaped card 20f.

FIG. 14C shows another potential embodiment of the apparatus in the shape of the apparatus 170c and in the shape of a cat wherein the jewelry 170c comprises only the scented card 20g and an attaching means 172 which could be a hook 172 for attaching the jewelry 20g to an earlobe (not shown) as an earring or which could be a clasping means for attaching the jewelry to as a charm to a charm bracelet (not shown) or necklace. Other forms of costume jewelry, including pieces connectable by connecting means to clothing, such as brooches, buttons, pins or lapel buttons can be easily envisioned.

Process for Manufacturing the Scented Material

The scented material used to produce the scented cards comprises a thermoplastic material having a fragrance. In general, the process of producing a scented sheet of material comprises providing a dry, particulate thermoplastic material, blending a chemical blowing agent and at least one fragrance or deodorizing agent into the thermoplastic material to form a mixture, heating the mixture in a thermoplastic extruder wherein the mixture is melted and the chemical blowing agent is activated thereby producing, in the plastic, gas pockets within which the fragrance is trapped. Following this, the process includes extruding the heated mixture from the extruder, forming a flat sheet of material from the extruded material, and at some point, trimming and cutting the sheet of material into cards having sizes and shapes suitable for insertion into holders or for other uses such as costume jewelry or refrigerator shelves as discussed above. The process may further comprise adding at least one coloring agent to the mixture prior to processing. The mixture is generally heated to that temperature sufficient to melt the thermoplastic material and activate the chemical blowing agent. This temperature may be approximately 280 degrees Fahrenheit, however, other temperatures may be utilized for different types of ingredients and different conditions.

In a preferred embodiment of the process, dry pellets of the copolymer resin ethylene-vinyl acetate are mixed with at least one fragrant oil, a chemical blowing agent and, optionally, a coloring agent. Ethylene-vinyl acetate is available commercially, for example, under the trade name ELVAX® from Du Pont Company. The preferred grade of ELVAX resin would be chosen from the group including ELVAX 470, 650, 660, 670 and 770, but is not restricted solely to these grades. A chemical blowing agent is one which, when activated at a particular temperature will evolve gas thereby providing bubbles within which is trapped the fragrance included in the blend. Azodicarbamide, is one example of a commercially-available chemical blowing agent which could be used in the blend. Azodicarbamide is available from SAFEFOAM. A variety of coloring agents or compounds such as Pantone are obtainable from suppliers such as Americhem, Inc., and can be optionally mixed with the resin blend to form scented cards having a variety of colors. One pound of color compound will color approximately 100 pounds of resin. Fragrant oils, available from a number of sources, including Berje, Inc., are combinable with mineral oil, which serves as a binding agent within the blend of resin, coloring agent, blowing agent and fragrance. The blend is then fed into an extrusion device (such as one available from Killion Extruders, Inc.) and heated to approximately 280° F., at which point the resin is melted and the chemical blowing agent is activated to evolve gas and form gas pockets within the plastic. As the blended ingredients move through the extruder the fragrance is trapped within the pockets of gas (although in certain embodiments in which a more rigid card or sheet is desired, the amount of chemical blowing agent may be reduced or altogether eliminated from the process). As the material proceeds through the extruder the temperature of the material is gradually reduced and as it exits, is caught by a sheet take-off machine (also available from Killion Extruders, Inc.). The take-off machine processes the extruded material through a series of chilled rollers which removes the remaining heat from the processed plastic as it is shaped into a flat uniform sheet. At the end of the line, a shearer cuts and trims the sheet of material into appropriately shaped cards, generally in a shape insertable into the various types of holders described earlier.

The result of the process is a, relatively rigid, but flexible solid card generally having a thickness of from one-thirty-secondths of an inch to three-sixteenths of an inch. In the preferred embodiment where the card is adapted to be inserted into a holder for being attached to the register of an air duct, the length of the card would generally be within the range of from three to four inches and the width would be in the range of from one and one-half inches to two and one-half inches, although these sizes may be somewhat smaller or larger depending on the circumstance. For example, in the circumstance in which the compartment to be scented is especially large and the size of the air duct register is unusually large, the dimensions of the scented card and the holder may be proportionately larger than the dimensions of a scenting device for a smaller register.

The scented sheet of material or card is also characterized as being substantially free of liquid, wherein the liquid is a free oil, containing fragrance, or moisture, wherein moisture is water bound within a colloidal support phase and a fragrance to create a semi-solid material such as a gel or cake-like material.

Changes may be made in the various elements and assembly described herein or the steps or the sequence of steps of the methods described herein without departing from the spirit and the scope of the invention as defined in the following claims.

What is claimed is:

1. An article removably connected to a register having a plurality of louvers wherein the register is operatively associated with an air outlet duct and where air flows through the air outlet duct and into a room for providing a scent in the room, comprising:

a holder being sized and shaped to be extended between a pair of the louvers in the register;

a card constructed of a relatively rigid thermoplastic material having scent incorporated therein, the card having a substantially flat upper surface and a substantially flat lower surface, a portion of the card being connectable to the holder; and connecting means connected to the holder, the connecting means being removably connected to one of the louvers in the register with the holder extending between a pair of the louvers in the register and into the register, air flowing through the air outlet duct and contacting the card for carrying scent from the card into the room.

2. The article of claim 1 wherein the card connected to the holder is substantially free of moisture.

3. The article of claim 1 wherein the card further comprises:

a first end side, a second end side, a first lateral side, and a second lateral side, the card having a thickness extending between the upper surface and the lower surface of the card and a width extending between the first lateral side and the second lateral side.

4. The article of claim 3 wherein the thickness of the card is defined further as being in a range from about one-thirty secondths of an inch to about three-sixteenths of an inch.

5. The article of claim 4 wherein the width of the card is defined further as being in a range from about one and one-half inches to about two and one-half inches.

6. The article of claim 4 wherein the card has a length extending between the first end side and the second end side, and wherein the length of the card is in a range from about three inches to about four and one-half inches.

7. An article operatively associated with a fan having fan blades for providing a scent in a room comprising:

a holder; and a card constructed of a relatively rigid thermoplastic material having scent incorporated therein, the card having a substantially flat upper surface and a substantially flat lower surface, a portion of the card being connectable to the holder; and connecting means connected to the holder, the connecting means being removably connected to one of the blades of the fan.

8. The article of claim 7 wherein the card is defined further as having a width and a thickness.

9. The article of claim 7 wherein the card further comprises a first end side, a second end side, a first lateral side, and a second lateral side, the card having a thickness extending between the upper surface and the lower surface of the card and a width extending between the first lateral side and the second lateral side.

10. The article of claim 7 wherein the thickness of the card is defined further as being in a range from about one-thirty secondths of an inch to about three-sixteenths of an inch.

11. The article of claim 10 wherein the width of the card is defined further as being in a range from about one and one-half inches to about two and one-half inches.

12. The article of claim 11 wherein the card has a length extending between the first end side and the second end side, and wherein the length of the card is in a range from about three inches to about four and one-half inches.

13. An article operatively associated with a refrigerator having an interior, the article for providing a scent comprising:

a holder encompassing an interior space, the holder having an upper surface and a lower surface with at least one opening being formed through the upper surface in communication with the interior space and at least one opening formed through the lower surface in communication with the interior space;

a card constructed of a relatively rigid thermoplastic material having scent incorporated therein, the card having a substantially flat upper surface and a substantially flat lower surface, a portion of the card being disposed in the interior space in the holder whereby air may pass through the openings in the upper and the lower surfaces of the holder and contact the card for carrying scent from the card; and connecting means connected to the holder and being removably connected to the refrigerator at a position within the interior of the refrigerator for providing a scent in the interior of the refrigerator.

14. The article of claim 13 wherein the card is defined further as having a width and a thickness.

15. The article of claim 13 wherein the card further comprises a first end side, a second end side, a first lateral side, and a second lateral side, the card having a thickness extending between the upper surface and the lower surface of the card and a width extending between the first lateral side and the second lateral side.

16. The article of claim 13 wherein the thickness of the card is defined further as being in a range from about one-thirty secondths of an inch to about three-sixteenths of an inch.

17. The article of claim 14 wherein the width of the card is defined further as being in a range from about one and one-half inches to about two and one-half inches.

18. The article of claim 14 wherein the card has a length extending between the first end side and the second end side, and wherein the length of the card is in a range from about three inches to about four and one-half inches.

19. The article of claim 18 wherein the interior space in the holder is defined further as having a length in a range of from about three and one half inches to about four and one half inches, a width in a range of from about one and three fourths inches to about two and three fourths inches, and a height in a range of from about one sixteenth of an inch to about one fourth of an inch.

20. An article for providing a scent comprising:

a holder having an upper part and a lower part, the upper part of the holder being detachable from the lower part of the holder and the upper part of the holder being reattachable to the lower part of the holder;

a card constructed of a relatively rigid thermoplastic material having scent incorporated therein, the card having a substantially flat upper surface and a substantially flat lower surface, the card being disposed between the upper part and the lower part of the holder when the upper part is detached from the lower part of the holder, and the lower part of the holder being reattached to the upper part of the holder with the card therebetween for holding the card in the holder.

21. The article of claim 20 wherein the card is defined further as having a width and a thickness.

22. The article of claim 20 wherein the card further comprises a first end side, a second end side, a first lateral side, and a second lateral side, the card having a thickness extending between the upper surface and the lower surface of the card and a width extending between the first lateral side and the second lateral side.

23. The article of claim 22 wherein the thickness of the card is defined further as being in a range from about one-thirty secondths of an inch to about three-sixteenths of an inch.

24. The article of claim 23 wherein the width of the card is defined further as being in a range from about one and one-half inches to about two and one-half inches.

25. The article of claim 23 wherein the card has a length extending between the first end side and the second end side, and wherein the length of the card is in a range from about three inches to about four and one-half inches.

26. An article for providing a scent comprising:

a housing substantially encompassing an interior space, a slot being formed through the housing in communication with the interior space in the housing;

a card constructed of a relatively rigid material having scent incorporated therein, the card having a substantially flat upper surface and a substantially flat lower surface, the card being removably inserted through the slot in the holder and disposed in the interior space in the holder; and means in the interior space in the housing for circulating air in the interior space over the card thereby scenting the air, and for passing the scented air from the housing.

27. The article of claim 26 wherein the housing further comprises an air in-take vent formed through the housing in communication with the interior space, air being drawn from outside the housing through the air in-take vent and into the interior space in the housing.

28. The article of claim 27 wherein the housing further comprises an air outflow vent, the air being passed over the card and passed through the air outflow vent from the housing.

29. The article of claim 28 wherein the card is defined further as having a width and a thickness and wherein the slot in the housing is defined further as having a width and a height, the width of the card being less than the width of the slot and the thickness of the card being less than the height of the slot in the housing.

30. The article of claim 28 wherein the card further comprises a first end side, a second end side, a first lateral side, and a second lateral side, the card having a thickness extending between the upper surface and the lower surface of the card and a width extending between the first lateral side and the second lateral side.

31. The article of claim 30 wherein the thickness of the card is defined further as being in a range from about one-thirty secondths of an inch to about three-sixteenths of an inch.

32. The article of claim 31 wherein the width of the card is defined further as being in a range from about one and one-half inches to about two and one-half inches.

33. The article of claim 31 wherein the card has a length extending between the first end side and the second end side, and wherein the length of the card is in a range from about three inches to about four and one-half inches.

34. The article of claim 33 wherein the interior space in the housing is defined further as having a length in a range of from about three and one half inches to about four and one half inches, a width in a range of from about one and three fourths inches to about two and three fourths inches, and a height in a range of from about one sixteenth of an inch to about one fourth of an inch.

35. The article of claim 34 wherein the slot in the housing is defined further as having a length in a range of from about one and three fourths inches to about two and three fourths inches, and a height in a range of from about one sixteenth of an inch to about one fourth of an inch, such that the width of the card is less than the width of the slot and the thickness of the card is less than the height of the slot.

36. An article for providing a scent comprising:

a holder encompassing an interior space, the holder having an opening formed therethrough in communication with the interior space; and a card having a substantially flat upper surface and a substantially flat lower surface, the card being constructed out of a relatively rigid, but flexible thermoplastic material with the card having a scent incorporated therein, a portion of the card being disposed in the interior space in the holder whereby air may pass through the opening in the holder and contact the card for carrying scent from the card.

37. The article of claim 36 wherein the card is defined further as having a width and a thickness.

38. The article of claim 36 wherein the card further comprises a first end side, a second end side, a first lateral side, and a second lateral side, the card having a thickness extending between the upper surface and the lower surface of the card and a width extending between the first lateral side and the second lateral side.

39. The article of claim 38 wherein the thickness of the card is defined further as being in a range from about one-thirty secondths of an inch to about three-sixteenths of an inch.

40. The article of claim 39 wherein the width of the card is defined further as being in a range from about one and one-half inches to about two and one-half inches.

41. The article of claim 39 wherein the card has a length extending between the first end side and the second end side, and wherein the length of the card is in a range from about three inches to about four and one-half inches.

42. The article of claim 41 wherein the interior space in the holder is defined further as having a length in a range of from about three and one half inches to about four and one half inches, a width in a range of from about one and three fourths inches to about two and three fourths inches, and a height in a range of from about one sixteenth of an inch to about one fourth of an inch.

43. An article operatively associated with a fan having fan blades for providing a scent in a room comprising:

- a card constructed of a relatively rigid thermoplastic material having scent incorporated therein, the card having a substantially flat upper surface and a substantially flat lower surface; and
- connecting means connected to the card, the connecting means being removably connected to one of the blades of the fan.

44. The article of claim 43 wherein the card is defined further as having a width and a thickness.

45. The article of claim 43 wherein the card further comprises a first end side, a second end side, a first lateral side, and a second lateral side, the card having a thickness extending between the upper surface and the lower surface of the card and a width extending between the first lateral side and the second lateral side.

46. The article of claim 45 wherein the thickness of the card is defined further as being in a range from about one-thirty secondths of an inch to about three-sixteenths of an inch.

47. The article of claim 46 wherein the width of the card is defined further as being in a range from about one and one-half inches to about two and one-half inches.

48. The article of claim 47 wherein the card has a length extending between the first end side and the second end side, and wherein the length of the card is in a range from about three inches to about four and one-half inches.

* * * * *